United States Patent [19]
de Chaffoy de Courcelles et al.

[11] Patent Number: 6,075,046
[45] Date of Patent: Jun. 13, 2000

[54] USE OF NEBIVOLOL AS AN ANTI-ATHEROGENIC

[75] Inventors: Didier Robert Guy Gabriël de Chaffoy de Courcelles, Beerse; Anne Simone Josephine Lesage, Halle-Zoersel; Josepha Eduarda Maria Francisca Leysen, Oud-Turnhout, all of Belgium

[73] Assignee: Janssen Pharmaceutica, N.V., Beerse, Belgium

[21] Appl. No.: 09/217,728

[22] Filed: Dec. 21, 1998

[30] Foreign Application Priority Data

Dec. 28, 1994 [EP] European Pat. Off. .............. 94203775

[51] Int. Cl.[7] .................................................. A01M 43/16
[52] U.S. Cl. ............................................................. 514/451
[58] Field of Search .............................................. 514/451

[56] References Cited

U.S. PATENT DOCUMENTS

| | | | |
|---|---|---|---|
| 5,759,580 | 6/1998 | Jans et al. ................................ | 424/489 |
| 5,874,461 | 2/1999 | Courcelles et al. ...................... | 514/451 |

FOREIGN PATENT DOCUMENTS 334 429  9/1989  European Pat. Off. .

OTHER PUBLICATIONS

G. Vandeplassche et al., "Cytoprotective Effects of Nebivolol", Drug Investigation, vol. 3 (Suppl.1):134–136, 1991.
L.M.A.B. Van Bortel et al. Antihypertensive treatment and vessel wall properties of large arteries, Besic Res. Cardiol, vol. 86, Suppl. 1, pp. 91–95, 1991.
Salvetti et al, "What effect Doe Blood Pressure Control Have on the Progression Towards Renal Failure?", American Journal of Kidney Diseases, vol. 21, No. 6, Suppl. 3, Jun. 1993, pp. 10–15.
P.M. Vanhoutte, "Endothelium, B –Blockers and Vascular Protection", Drug Investigation 3 (Suppl.1): 201–203, 1991.

*Primary Examiner*—Theodore J. Criares
*Attorney, Agent, or Firm*—Mary A. Appollina

[57] ABSTRACT

This invention relates to the use of an $\alpha,\alpha'$-iminobis (methylene)bis[2-chromanmethanol] derivative for the manufacture of a medicament for the therapeutic or prophylactic treatment of humans suffering from or prone to degenerative diseases and conditions of the vascular and nervous system which are associated with oxidative stress.

7 Claims, No Drawings

USE OF NEBIVOLOL AS AN ANTI-ATHEROGENIC

The present invention is concerned with the use of an α,α'-iminobis(methylene)bis[2-chromanmethanol] derivative for the manufacture of a medicament for the therapeutic or prophylactic treatment of humans suffering from aging of, or degenerative diseases of the vascular and nervous system which are associated with oxidative stress.

α,α'-Iminobis(methylene)bis[2-chromanmethanol] derivatives are disclosed in EP-0,145,067 as β-1 blocking agents having therapeutic potential for treating hypertension. Nebivolol, which consists of a racemic mixture of (RSSS) and (SRRR) α,α'-iminobis(methylene)bis[6-fluoro-2-chromanmethanol] is generically disclosed therein. Nebivolol is disclosed specifically in EP-0,334,429, and therein the (SRRR) enantiomer is shown to be a potent and selective β-1 blocking agent, whereas the (RSSS) enantiomer is shown not to be a potent β-1 blocking agent, but a potentiator for a series of antihypertensive agents such as atenolol, propanolol, prazosin, hydralazine and, interestingly, also its own (SRRR) enantiomer. In the meantime subsequent investigations have shown that several beneficial haemodynamic effects of nebivolol which distinguish it from other β-1 blocking agents, e.g. that it acutely lowers blood pressure in spontaneous hypertensive rats, decreases total peripheral vascular resistance and augments stroke volume in anaesthesized doge, are also largely attributable to the (RSSS) enantiomer.

Experiments now show that α,α'-iminobis(methylene)bis[2-chromanmethanol] derivatives have potent antioxidant activity both in vitro and in vivo. Apparently, this is only the second group of β-1 blockers after carvedilol and its metabolites to exhibit antioxidant properties in vitro and in vivo, with this difference that the α,α'-iminobis(methylene)bis[2-chromanmethanol] derivative would appear to be more potent. In view of their antioxidant properties, α,α'-iminobis(methylene)bis[2-chromanmethanol] derivatives have therapeutical utility in the treatment of degenerative diseases as well as aging of the vascular and nervous system which are caused by oxidative stress.

Consequently, the present invention is concerned with the use of α,α'-iminobis(methylene)bis[2-chromanmethanol] derivatives, the pharmaceutically acceptable acid addition salts, the stereochemically isomeric forms, and any mixtures of said derivatives, salts and stereoisomers, for the manufacture of a medicament for the therapeutic or prophylactic treatment of humans suffering from aging of, or degenerative diseases of the vascular and nervous system which are associated with oxidative stress, said derivatives having the formula (I):

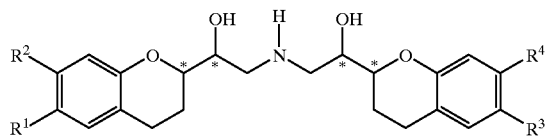

wherein $R^1$ and $R^3$ each independently represent fluoro, hydroxy or hydrogen, $R^2$ and $R^4$ each independently represent hydrogen or hydroxy, and each asterisk indicates a stereogenic center.

The invention also concerns a method of treating patients suffering from aging of or degenerative diseases of the vascular and nervous system which are associated with oxidative stress, by administering to said patients an amount of an α,α'-iminobis(methylene)bis[2-chromanmethanol] derivative effective in improving, halting, retarding or palliating the course and/or effects of said aging and degenerative diseases.

The compounds wherein $R^1$ and $R^3$ represent hydroxy, and $R^2$ and $R^4$ represent hydrogen, were thought to be the main metabolites formed from the corresponding compounds wherein $R^1$ and $R^3$ represent fluoro, but very recent findings show that they are not. Nevertheless, these pseudo-metabolites do have potent anti-oxidant activity.

Specific compounds according to the invention include:
(RSSS) and (SRRR) α,α'-iminobis(methylene)bis[6-fluoro-2-chroman-methanol], the racemic mixture of which is generally known as nebivolol, its individual enantiomers, (RSSS) and (SRRR) α,α'-iminobis(methylene)bis[6-hydroxy-2-chroman-methanol];
[(RSSS)+(RSRR)+(SRSS)+(SRRR)]-α-[[[2-(chroman-2-yl)-2-hydroxyethyl]amino]methyl]-6-hydroxy-2-chroman-methanol ethanedioate (1:1);
[(SRSR)+(SRRS)+(RSSR)]-α,α'-iminobis(methylene)bis[6-hydroxy-2-chromanmethanol], and
[(RRSR)+(RRRS)+(SSSR)+(SSRS)]-α-[[[2-(chroman-2-yl)-2-hydroxyethyl]amino]methyl]-6-hydroxy-2-chroman-methanol ethanedioate (1:1).

The compounds of formula (I) may be prepared following the procedures described in EP-0,145,067 and EP-0,334,429. As they have basic properties, these compounds may be converted into their pharmaceutically acceptable acid addition salt forms by treatment with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicyclic, pamoic and the like acids. The term addition salt as used hereinabove also comprises the solvates which the compounds of formula (I) as well as the salts thereof, are able to form. Such solvates are for example hydrates, alcoholates and the like. The preferred acid addition salt of nebivolol is the hydrochloride salt. Salts which are not pharmaceutically acceptable may be useful in the preparation of the compounds of formula (I) and of compositions comprising such compounds.

Oxidative stress refers to phenomena related to the action, in particular the deleterious effects, of endogenous strong oxidants within tissue. Endogenous strong oxidants are for example superoxide $(O_2^-)^\bullet$, hydrogen peroxide $(H_2O_2)$ and the hydroxyl radical $(HO^\bullet)$. The tissue may be central, peripheral or medullar, and in particular belongs to the vascular system, the nervous system, the kidneys, the pancreas, the parathyroid glands and the gonads. Oxidative injury to tissue cell is attributed to lipid peroxidation, leading to changes in cell membrane integrity and function. Endothelial injury by oxygen derived free radicals is nowadays generally considered to be a key step in the initiation and progression of atherosclerosis and related vascular diseases.

Therapeutic treatment comprises the administration of a compound of formula (I) in an amount effective in improving halting, retarding or palliating the course and/or effects of degenerative diseases of the vascular and nervous system. Prophylactic treatment comprises the administration of such a compound in an amount effective in preventing or delaying the onset and evolution of aging of, or degenerative diseases of the vascular and nervous system.

The antioxidant activity of α, α'-iminobis(methylene)bis[2-chromanmethanol] derivatives can be demonstrated in vitro by their ability to scavenge free radicals (hydroxyl, superoxide and nitric oxide radicals) and thus prevent radical-mediated lipid peroxidation and cytotoxicity. In cultures of neuronal cells, they can effectively substitute the known endogenous antioxidant vitamin E (α-tocopherol). The compounds also mimic the action of superoxide dismutase (SOD) by scavenging superoxide $(O_2^-)^·$. The antioxidant activity of different stereoisomers of the compounds of formula (I) is comparable. The antioxidant activity of the compounds of formula (I) is proportional with the number of hydroxy groups present.

A particular interesting finding is that compounds wherein at least one of $R^{1-4}$ represents hydroxyl, dose-dependently inhibit the formation of oxidized human low density lipoprotein (ox-LDL) in the micromolar range in vitro. Oxidized-LDL is implicated in atherogenesis, as well as the formation of oxidized membrane lipids. FIG. 1 shows the phases discerned in the formation of oxidized LDL; FIG. 2 shows the formation of oxidized LDL in vitro in control circumstances and in the presence of active drugs. Since hydroxylation is an important enzymatic reaction in the metabolism of nebivolol one can foresee that in view of the antioxidative effect of its hydroxy analogues, nebivolol should have important protective effects against oxidative damage in vivo.

This is corroborated by a most unexpected observation in an in vivo test namely, that in test animals treated chronically with nebivolol, the normal aging of the vascular system as seen in the control animals is suppressed, i.e. that the aging process in treated animals is manifestly retarded.

Diseases and conditions of the vascular and nervous system which are associated with oxidative stress and which are considered to be susceptible to treatment with the compounds of formula (I) are normal and pathological degeneration of the vascular system such as atherogenesis, atheromatosis (fatty degeneration of the endothelium of arteries), arteriosclerosis, atherosclerosis, vascular hypertrophy associated with hypertension, hyperlipoproteinaemia, and normal vascular degeneration through aging; vasculopathology of the gonads and pancreas; parathyroidal reactive hyperplasia; and chronic renal disease; in neoplastic diseases; and in inflammatory diseases.

Further, the compounds of formula (I) may also have therapeutic value in preventing or treating neuronal loss from the nervous system, in particular the peripheral nervous system, which is associated with oxidative damage or injury, e.g. in thromboembolic stroke, cerebral stroke, haemorrhagic stroke, cerebral ischaemia, cerebral vasospasm, cerebral aging, cerebral or spinal trauma, cardiac arrest, arterial hypotension, cardiac or pulmonary surgery, severe hypoglycaemia, anoxia, hypoxia, perinatal asphyxia; and in alleviating neurodegenerative disorders wherein oxidative metabolic processes play a role such as, Huntington's chorea, Alzheimer's disease, senile dementia, Pick's disease, Korsakoff's disease, olivoponton cerebellar atrophy, amyotrophic lateral sclerosis, Parkinson's disease, Down's syndrome, glutaric acidaemia, epilepsy, convulsive states, multi-infarct dementia, viral-infection induced neurodegeneration, e.g. neuro-AIDS encompassing dementia, cognitive difficulties, neuro- and myopathies associated with HIV infection, rabies, measles and tetanus.

Atherogenesis is a complex process characterized by the accumulation of cholesterol in macrophages resident in the arterial wall. Macrophages take up oxidized LDL via the scavenger receptor which is contrast to the normal-LDL-receptor is not regulated by the cellular cholesterol content. The lack of regulatory mechanism results in cellular cholesterol accumulation and foam-cell formation. Oxidized LDL has been discovered in vivo in areas of proximity to the atherosclerotic lesion (for a review, see Jackson, R. L. et al. (1993), Medicinal Research Reviews 13, 161–162). LDL oxidation involves lipid peroxidation, aldehyde formation, protein fragmentation and consumption of LDL particle-associated vitamin E. Auto-antibodies against LDL have been identified in man. Their titre is an independent predictor of the progression of carotid atherosclerosis (Salonen, J. T. et al. (1992), The Lancet 339, No 8798, 883–887). Furthermore, susceptibility to LDL oxidation is associated with severity of coronary atherosclerosis (Regnström, J. et al. (1992), The Lancet 339, No 8803, 1183–1186). Any antioxidant property attributed to a cardiovascular protective drug in addition to its other pharmacological properties enhances its therapeutic effect in preventing the progression of the atherosclerotic process.

The data in Example 1 hereinafter prove that the hydroxy analogues of nebivolol have a far-reaching antioxidant effect on human LDL. The concentrations used in vitro were high ($2 \mu M$) but of no relevance for comparison to the in vivo condition. Indeed, both vitamin E and the known antioxidant and hipolipidemic agent probucol, have been shown to be incorporated into the lipid phase of the LDL particle over a time course spanning weeks (Reaven, P. D. et al. (1992), Artheriosclerosis and Thrombosis, 12, No 3, 318–324; Kagan, V. E. et al. (1992), J. Lip. Res., 33, 385–397). The short duration of the experiment in Example 1 did not simulate this in vivo situation. The distribution of the drugs between the aqueous phase and the lipid phase of the LDL particles probably did not reach equilibrium, so that the antioxidative capacity of these lipid-soluble drugs was underestimated, as evidenced by the extremely high concentration that was required of vitamin E, the reference compound. Qualitatively, the effect of the nebivolol hydroxy analogues and of vitamin E is similar. Both delay the oxidation of LDL, oxidation starting only after consumption of the antioxidants present in the assay system.

Pharmaceutical compositions of the compounds of formula (I) suitable as medicaments according to the present invention comprise one or more excipients or carriers as known in the art. By appropriately selecting one or more of these excipients or carriers, the pharmaceutical compositions are adapted for oral, rectal, vaginal, topical, parenteral (including intramuscular, subcutaneous and intravenous) or implant administration or in a form suitable for administration by inhalation or insufflation. The formulations may, where appropriate, be conveniently presented in discrete dosage units.

Processes of preparing such compositions are well known in the art and are characterized in that the active ingredient and the excipient are ultimately mixed with one another. All processes include the step of bringing into association the active compound with liquid carriers or finely divided solid carriers or both and then, if necessary, shaping the product into the desired formulation.

For oral administration, the pharmaceutical compositions may take the form of solid dose forms, for example, tablets or capsules prepared by conventional means with pharmaceutically acceptable excipients such as binding agents (e.g. pregelatinised starch, poly-vinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For topical administration in the mouth, the pharmaceutical compositions may take the form of buccal or sublingual tablets, drops or lozenges formulated in conventional manner.

For topical administration to the epidermis the compounds of the invention may be formulated as creams, gels, ointments or lotions or as transdermal patches. Such compositions may, for example, be formulated with an aqueous or oily base with the addition of suitable thickening, gelling, emulsifying, stabilising, dispersing, suspending, and/or colouring agents.

The compounds of formula (I) may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of formula (I) may be formulated for parenteral administration by injection, conveniently intravenous, intramuscular or subcutaneous injection, for example by bolus injection or continuous intravenous infusion. Formulations for injection may be presented in unit dosage form e.g. in ampoules, or in multidose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water.

The compounds of formula (I) may also be formulated in rectal compositions such as suppositories or retention enemas, e.g. containing conventional suppository bases such as cocoa butter or other glycerides.

For intranasal administration the compounds of formula (I) may be used, for example, as a liquid spray, as a powder or in the form of drops.

For administration by inhalation the compounds of formula (I) are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, 1,1,1,2-tetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch. Any of the pharmaceutical compositions described above may be presented in a conventional manner associated with controlled release forms.

In order to increase the bio-availability of the compounds of formula (I), they may be formulated advantageously with appropriate cyclodextrins. Appropriate cyclodextrins are α-, β-, γ-cyclodextrins, or ethers, or mixed ethers thereof wherein one or more of the hydroxy groups of the anhydroglucose units of the cyclodextrin are substituted with $C_{1-6}$alkyl, particularly methyl, ethyl or isopropyl; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl.

Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The most preferred cyclodextrin derivative for use in the compositions of the present invention is 2-hydroxypropyl-β-cyclodextrin having an average molar substitution (M.S.) in the range of from 0.35 to 0.50 (determined by mass spectroscopy) and containing less than 1.5% unsubstituted β-cyclodextrin. M.S. values determined by NMR or IR preferably range from 0.55 to 0.75.

The pharmaceutical compositions may consist of only the compound of formula (I) and the cyclodextrin or cyclodextrin derivative. This solid form can conveniently be prepared by lyophilization of an aqueous solution, or also by co-precipitation. Such form is particularly useful for reconstitution with water, saline or an aqueous solution of the cyclodextrin, or for compounding with non-pharmaceutical solids, in particular food.

Preferably, the pharmaceutical compositions according to the invention are suitable for oral administration.

The compositions may advantageously be presented in discrete dose units, especially in unit dosage forms. A convenient unit dose formulation contains the active ingredient in an amount of from 0.1 to 100 mg. The amount of a compound of formula (I) required as daily dose in treatment will vary not only with the particular compound selected, but also with the route of administration, the nature of the condition being treated and the age, weight and condition of the patient and will ultimately be at the discretion of the attendant physician. In general, however, a suitable dose will be in the range of from about 0.1 to about 20 mg per day. A suitable daily dose for use in prophylaxis will generally be in the same range.

The desired dose may conveniently be presented in a single dose or as divided doses administered at appropriate intervals, for example as two, three, four or more sub-doses per day. The daily dose of nebivolol can be administered in single dose (o.d.), because such a regimen yields effective plasm levels over a period of 24 hours. Due to the formation of active metabolites with increased antioxidant efficiency, the antiatherogenic effect of nebivolol will increase upon reiterated or chronic administration until a steady state is reached.

The compounds of formula (I) may also be used in combinations with other blood pressure lowering agents, or with other therapeutic agents, for example, hypolipaemics, hypolipidemics, cholesterol lowering agents, ACAT inhibitors or antioxidants. The invention thus provides, in a further aspect, a combination comprising a composition as defined herein, together with another therapeutically active agent, in particular another blood pressure lowering agent or a hypolipaemic, hypolipidemic, cholesterol lowering agent, ACAT inhibitor or antioxidant. The combination may be administered separately, i.e. simultaneously, concurrently or consecutively by any of the routes described above, or the combination may also be presented in the form of one pharmaceutical formulation. Thus, a pharmaceutical product comprising (a) a compound of formula (I) and (b) another therapeutic agent as defined hereinbefore, as a combined preparation for simultaneous, separate or sequential use in the therapeutic or prophylactic treatment of humans suffering from aging of, or degenerative diseases of the vascular or nervous system which are associated with oxidative stress, comprises a further aspect of the invention. Such a product may comprise a kit comprising a container containing a pharmaceutical composition of a compound of formula (I), and another container comprising a pharmaceutical composition of the second therapeutic agent. The product with separate compositions of the two active ingredients has the advantage that appropriate amounts of each component, and timing and sequence of administration can be selected in function of the patient.

Suitable therapeutic agents for use in the combinations defined above include, for example blood pressure lowering agents, in particular β-1 blocking agents such as for example, atenolol, celiprolol, propanolol; hypolipaemics, i.e. medicines useful in lowering low density lipoprotein (LDL) or cholesterol such as, for example, HMG CoA reductase inhibitors e.g. lovastatin, fluvastatin, pravastatin, simvastatin and the like; gemfibrozil; zaragozic acid; or antioxidants e.g. probucol, vitamin E (α-tocopherol), or in particular compounds that combine several of the above-mentioned physiological properties, e.g. carvedilol, verapamil, diltiazem, vitamin C (ascorbic acid or a salt thereof).

When compounds of formula (I) are used in combination with a second therapeutic agent, the dose of each compound may vary from that when the compound is used alone. Thus when compounds of formula (I) are used together with a second therapeutic agent the dose of each compound may be the same or more commonly, lower, than that employed when the compound is used alone. Appropriate doses will be readily appreciated by those skilled in the art.

EXAMPLE 1

In Vitro Oxidation of Human LDL

Human venous blood was collected on EDTA (2.68 mM final concentration). Plasma was isolated by centrifugation. NaBr (37.3 mg/ml) was added and solubulized (final density 1.036 g/ml). Centrifuge tubes were first filled to a level corresponding to ⅔ of their maximal volume, further filled with a NaBr solution of 1.036 g/ml and then centrifuged for 18 hours at 45000 rpm in a 50 Ti rotor (Beckmann). After centrifugation, floating lipoproteins were discarded. The remaining solution was adjusted to a density of 1.055 g/ml. Filling of the centrifuge tubes and centrifugation were repeated as described above. After centrifugation, floating LDL was dialysed against a buffer containing 127 mM NaCl, 8 mM $Na_2HPO_4.2H_2O$, 2.7 mM KCl and 1.47 mM $KH_2PO_4$ at pH 7.4. After dialysis, LDL was filtered though a Millipore filter (0.45 μM) and protein content was determined. A dilution of 25 μg/ml was prepared with a millipored dialysis buffer. Oxidation was determined in a Pharmacia Ultraspec III spectrophotometer. Conjugated diene formation was registered at 234 nm. Two μl of a drug or solvent (DMSO) were added to Eppendorf tubes followed by 1 ml of LDL (25 μg/ml) and these substances were gently mixed and centrifuged for 1 min at 1300 g. The solution was pipetted in a Quartz cuvet that was thermostatised in the spectrophotometer at 37° C. After equilibration, the oxidation reaction was started by the addition of $CuSO_4$ (final concentration 10 μM). Absorbance was measured every 3 minutes during the time course of the experiment. The absorbance at 234 nm was divided into three phases: a lag phase, a propagation phase and a decomposition phase. The lag phase was defined as the intercept with the baseline of the tangent of the slope of the absorbance curve of the propagation phase. The rate of oxidation was defined as the tangent of the slope. $T_{max}$ was defined as the time required to attain the maximum absorbance between the propagation and the decomposition phase. The absorbance at $t_{max}$ minus the absorbance at $t_0$ was taken as an indicator of the total amount of dienes formed. To verify the reproducibility of the assay, a reference LDL sample was prepared and kept in darkness under nitrogen at 4° C. This reference sample was included in every oxidation experiment. LDL was isolated from 23 subjects. Plasma cholesterol ranged from 156 to 278 mg/dl (mean 213 mg/dl), triglycerides ranged from 47 to 328 mg/dl (mean 191 mg/dl) and phospholipids ranged from 178 to 327 mg/dl (mean 231 mg/dl).

2 hydroxy analogues of nebivolol are:

[(RSSS)+(RSRR)+(SRSS)+(SRRR)]-α-[[[2-(chroman-2-yl)-2-hydroxyethyl]amino]-methyl]-6-hydroxy-2-chroman-methanol ethanedioate (1:1), and

[(SRSR)+(SRRS)+(RSSR)]-α,α'-iminobis(methylene)bis[6-hydroxy-2-chroman-methanol]. $T_{max}$, and the lag time are both increased and the rate of oxidation is decreased. In vitro, nebivolol has no antioxidative effect. Vitamin E as a reference compound did not show any anti-oxidant effect at a concentration lower than 10 μM (results not shown). The $t_{max}$ at 20 μM vitamin E was close to the $t_{max}$ for the 2 μM hydroxymetabolites of nebivolol in our experimental conditions. The rate of oxidation, the initial absorbance and the total amount dienes were not affected by vitamin E. In conclusion, the hydroxy metabolites of nebivolol have an antioxidative effect on human LDL in vitro. Nebivolol therefore might have important protective effects against oxidative damage in vivo of the type that occurs in atherosclerosis, inflammation and cancer.

EXAMPLE 2

In-Vivo Anti-Atheromatic Effect of Nebivolol

In order to verify whether nebivolol had any effect on age-associated vascular pathology, a number of rats were administered nebivolol orally at dosages of 0 (carrier-only), 2.5, 10 and 40 mg/kg during 24 months. As a carrier there was used 2-hydroxy-propyl-β-cyclodextrin which improves the bioavailability of nebivolol. At each dose a male and female group of 50 were entered in the 2 year study. A male and a female control group of 50 which did not receive any nebivolol was also included in the study. The test animals were autopsied and observed for histological non-neoplastic changes. The following histological features which can be related to vascular degeneration or aging were observed in particular:

vasculopathy of the abdominal mesothelia, pancreas, and testis, focal and diffuse hyperplasia of the parathyroid gland, and the renal histology, in particular the number of basophilic tubuli, evidence for chronic renal disease and for mineralization.

Histopathological observations received a score from 0 to 3 as follows:

0: no histological change
1: slight histological change
2: moderate histological change
3: severe histological change.

For each observation a mean score was calculated. The observed ratings were analysed using the Mann-Whitney U test (two tailed probability) to detect statistically significant differences between the control groups and the treated groups. These ratings are summarized in the table below. Significance computed by Mann-Whitney U test two-tailed: *p<0.05 p<0.01 *p<0.001.

TABLE 1

| Histological change | Dosage group (mg/kg) | | | | |
|---|---|---|---|---|---|
| | Control | Vehicle | 2.5 | 10 | 40 |
| Males | | | | | |
| Abdominal mesothelia: vasculopathy | 2.50 | — | — | — | 0.00 * |
| Kidney: | | | | | |
| basophilic tubuli | 0.10 | 0.12 | 0.18 | 0.18 | 0.60*** |
| chronic disease | 1.68 | 1.40 | 1.32* | 1.24* | 0.66*** |
| Pancreas: vasculopathy | 0.30 | 0.18 | 0.04 | 0.02* | 0.00*** |
| Parathyroid gland: | | | | | |
| diffuse hyperplasia | 0.18 | 0.14 | 0.08 | 0.15 | 0.02* |
| focal hyperplasia | 0.16 | 0.08 | 0.04 | 0.02* | 0.00** |
| Testis vasculopathy | 0.52 | 0.48 | 0.20* | 0.08** | 0.02*** |
| FEMALES | | | | | |
| Kidney: | | | | | |
| basophilic tubuli | 0.04 | 0.14 | 0.18 | 0.18* | 0.42*** |
| chronic disease | 1.04 | 0.76 | 0.88 | 0.92 | 0.78 |
| mineralization (parenchum/pelvis) | 0.96 | 0.74 | 0.84 | 0.64* | 0.14*** |
| Pancreas vasculopathy | 0.12 | 0.04 | 0.04 | 0.02 | 0.00* |

EXAMPLE 3

Primary embryonic hippocampal cultures were prepared essentially as described previously (Pauwels et al., Van Aschouw, H. P., Peeters, L., Moeremans, M., Leysen, J. E. (1992) Chronic treatment with sabeluzole protects cultured rat brain neurons from the neurotoxic effects of excitatory amino acids. Synapse, 12:271–280). Hippocampal formations of rats at embryonic day 17 were dissected and dissociated in 0.05% trypsin, 0.1 mg/ml DNase I in DMEM (Dulbecco Modified Eagle Medium). Heat-inactivated horse serum (HS) was added to a concentration of 4%, and the cells were centrifuged, washed with DMEM, and resuspended in DMEM/Ham's F12 (3:1) containing 10% HS. The cells were plated at a density of $4 \times 10^5$ cells/cm$^2$ in poly L-lysine (0.001%) precoated multiwell-24 plates. On day 1 in culture, the medium was changed to chemically defined CDM-R12 medium (DMEM-HEPES/Ham's F12 (3:1) containing 0.26% bovine serum albumin, 30 nM sodium selenite, 3 nM 3,3',5 triiodo-L-thyronine, 0.35 $\mu$M retinol, 0.3 $\mu$M retinol acetate, 2,3 $\mu$M DL-a-tocopherol, 2.1 $\mu$M DL-a-tocopherol acetate, 3.6 $\mu$M linolenic acid, 3.6 $\mu$M linoleic acid, 0.125% human transferrin, 20 nM progesterone, 57.7 nM corticosterone, 49 U/l insulin, 0.4 $\mu$M biotin, 10 $\mu$M L-carnitine, 83 $\mu$M D(+)-galactose, 3.3 $\mu$M glutathione, 10 $\mu$M ethanolamine, 0.1 mM putrescine; Romijn, H. J., van Huizen, F., Wolters, P. S. (1984) Towards an improved serum-free, chemically defined medium for long-term culturing of cerebral cortex tissue. Neurosci. Behav. Rev., 8:301–334). Acute and prolonged pretreatment of the cultures was essentially as described previously (Pauwels et al., 1992). Drugs were dissolved, and diluted in 10% or 1% hydroxypropyl-β-cyclodextrin such that the final concentrations of the solvent in the acute and chronic exposures were 0.1% and 0.01% respectively. Compound A as used in the following examples is [(RRSR)+(RRRS)+(SSSR)+(SSRS)]-α-[[[2-(chroman-2-yl)-2-hydroxy-ethyl]amino]methyl]-6-hydroxy-2-chroman-methanol ethanedioate (1:1).

For acute treatment, drug, or solvent was added to the cultures on day 7. After 20 min the medium was replaced with 200 $\mu$l chemically defined DMEM medium (the same composition of CDM-R12 medium but without Ham's F12) (control), or chemically defined DMEM medium containing the oxidative stress trigger. Oxidative stress triggers used were 1 mM sodium nitroprusside (SNP, a nitric oxide radical generating compound), or 7.5–10 mM diethyldithiocarbamate (DDTC, a superoxide dismutase inhibitor) and the test compound.

For prolonged pretreatment experiments, drug (concentration range 0.1 nM–10 $\mu$M) was added to the serum-free medium on days 1 and 4 of the culture. On day 7, the cultures were washed once with DMEM, and incubated with 0.2 ml chemically defined DMEM medium for 2 h at 37° C. The cells were washed and the medium was replaced by 0.2 ml chemically defined DMEM medium (control), or chemically defined DMEM medium containing the oxidative stress trigger (see above).

For both the acute experiment and the prolonged pretreatment experiment, extracellular and intracellular LDH (lactate dehydrogenase) activities were measured spectrophotometrically at 340 nm with an EPOS Analyzer 5060, according to the method of Bergmeyer (Bergmeyer, H. U. (1974) Biochemical reagents. In: Methods of Enzymatic Analysis. H. U. Bergmeyer, eds. Academic Press, New York, 2nd Ed., pp. 480–242). Extracellular LDH activity in the culture medium and cytoplasmic LDH activity measured after lysis of the cells in 1 ml H$_2$O, were used to calculate total LDH activity and % released LDH. % Neuroprotection refers to % inhibition of LDH release, where oxidative stress trigger-induced LDH release is defined as 0% protection, and basal (control) level of LDH release is defined as 100% protection.

For vitE depletion experiments, primary cultures were set up as above, but on day 1 in culture, the medium was changed to chemically defined CDM-R12 medium with (control) or without DL-a-tocopherol (VitE) and DL-a-tocopherol acetate, in the presence or absence of test compound. When vitE was omitted from the culture medium, severe cell death was observed at 4 days in vitro. Addition of compounds could rescue the cultures. Culture survival was measured by means of cytoplasmic LDH activity. % vitE complementation refers to % cytoplasmic LDH, were LDH levels as high as those seen in vitE containing cultures was defined as 100%, and LDH levels as low as seen in the vitE depleted cultures was defined as 0%. The EC$_{50}$ for complementation of vitE refers to the concentration of the compound required to restore culture survival to 50% of the survival seen for the culture grown in vitE supplemented medium. Seven concentrations of each compound were tested in triplicate, the number of independent experiments is indicated in the table, and the mean EC$_{50}$- value±SD was calculated.

Table 2: VitE complementation test: effect of nebivolol derivatives, screening data Table 3: VitE complementation test: potency of Compound A Table 4: In vitro neuroprotection of nebivolol, Compound A, and carvedilol against nitric oxide and superoxide radicals Primary neuronal cultures depend on the presence of the antioxidant vitE in the culture medium for survival in vitro. When vitE depleted medium is used to grow the cultures, survival drops to ±20% of control. Compounds with antioxidative properties are able to complement the lack of vitE, and as such can when added to the culture medium, rescue vitE devoid cultures. Several nebivolol derivatives were tested at $10^{-7}$ M and $10^{-6}$ M in the vitE depletion test on primary neuronal cultures. Compound A, nebivolol, l-nebivolol and d-nebivolol were all able to rescue survival of vitE depleted cultures to a certain extent (Table 2).

Compound A was the most potent compound: complete rescue of primary neuronal cultures grown in VitE depleted medium was seen at $10^{-6}$ M (Table 2). The concentration of Compound A at which the culture was rescued to 50% of control (control is a culture grown in medium containing 4.4 µM vitE) was 126±88 nM (Table 3).

Treatment of cultures with the superoxide dismutase inhibitor DDTC, and the nitric oxide donor SNP result in radical ($O_2^{-\cdot}$ and $NO^{\cdot}$ respectively) mediated neurotoxicity.

Compounds with antioxidative properties are able to protect cultures from radical mediated neurotoxicity, when added shortly before and during the trigger (acute treatment), or when added for 6 days before the trigger (prolonged pretreatment). From Table 3 it is clear that nebivolol and Compound A can confer neuroprotection on the cultures against DDTC or SNP in one or the other treatment paradigm. The underlying mechanism for treatment-dependent neuroprotection is unknown to date. The albeit partial protection seen with nebivolol and Compound A against SNP and DDTC is however not observed with carvedilol, which makes nebivolol and Compound A superior drugs in this respect.

TABLE 2

VitE complementation test : effect of nebivolol derivatives, screening data.

| Compound | Concentration (M) | % vitE complementation (number of tests) |
|---|---|---|
| Compound A | $10^{-7}$ | 27 ± 28 (16) |
|  | $10^{-6}$ | 85 ± 21 (16) |
| nebivolol | $10^{-7}$ | 29 ± 29 (15) |
| (RSSS, SRRR) | $10^{-6}$ | 29 ± 28 (15) |
| l-nebivolol | $10^{-7}$ | 22 ± 20 (13) |
| (SRRR) | $10^{-6}$ | 24 ± 26 (13) |
| d-nebivolol | $10^{-7}$ | 12 ± 17 (7) |
| (RSSS) | $10^{-6}$ | 19 ± 22 (7) |

Neuronal primary hippocampal cultures were grown in the absence of the survival factor vitE, which resulted in severe celldeath. When nebivolol derivatives were administered during culture, the cultures could be rescued to a certain extent. 100% vitE complementation refers to the survival of a cell culture which is indifferent from a vitE containing cell culture.

TABLE 3

VitE complementation test : potency of hydroxynebivolol

| Compound | mean $EC_{50}$ ± SD (number of dose responses) |
|---|---|
| Compound A | 126 ± 88 nM (5) |

Neuronal primary hippocampal cultures were grown in the absence of the survival factor vitE, which resulted in severe celldeath. When hydroxynebivolol was administered during culture, the cultures could be rescued. The $EC_{50}$ refers to the concentration at which the culture is rescued for 50%, as measured by cytoplasmic LDH activity.

TABLE 4

In vitro neuroprotection by nebivolol, Compound A, and carvedilol against nitric oxide and superoxide radicals
% neuroprotection, mean ± SD
(number of independent cultures)

| Compound | Trigger | Prolonged pretreatment | | Acute treatment | |
|---|---|---|---|---|---|
|  |  | $10^{-7}$M | $10^{-6}$M | $10^{-7}$M | $10^{-6}$M |
| nebivolol | DDTC | NA | 37 ± 23 | 32 ± 28 | 29 ± 16 |
| (RSSS, SRRR) |  | (2) | (2) | (5) | (7) |
|  | SNP | 26 ± 13 | 36 ± 18 | NA | NA |
|  |  | (2) | (3) | (2) | (2) |
| Compound A | DDTC | NA | NA | 35 ± 32 | 30 ± 28 |
|  |  | (2) | (2) | (5) | (6) |
|  | SNP | 39 ± 13 | 38 | NA | NA |
|  |  | (2) | (1) | (2) | (2) |
| carvedilol | DDTC | NA | NA | NA | NA |
|  |  | (2) | (2) | (1) | (4) |
|  | SNP | NA | NA | NA | NA |
|  |  | (1) | (1) | (1) | (1) |

Neuronal primary hippocampal cultures were grown in CDM-R12 medium for 7 days. Test compounds were either administered on days 1 and 4 of culture (prolonged pretreatment) or on day 7 of culture (acute treament). The oxidative stress trigger was administered on day 7, and neuroprotection was calculated based on inhibition of LDH release. NA, signifies not active, i.e. scoring <25% neuroprotection.

EXAMPLE 4

Competitive inhibition by glutamate of cystine uptake in certain cells leads to glutathione depletion and oxidative stress. This oxidative stress model has been described for glial C6 glioma cells (Kato et al., 1992. A mechanism for glutamate toxicity in the C6 glioma cells involving inhibition of cystine uptake leading to glutathione depletion. Neurosci. 48:903–914) and for the neuronal cell line N18RE105 (Murphy et al., 1989. Glutamate toxicity in a neuronal cell line involves inhibition of cystine transport leading to oxidative stress. Neuron 2:1547–1558).

Cell Culture

The C6 glioma cell line (American Type Culture Collection, CCL 107) was cultivated in DMEM supplemented with 2 or 4 mM glutamine, 1 mM pyruvate and 5 or 10% heat-inactivated foetal calf serum. Cultures were maintained at 37° C. in an air/5~10% $CO_2$, water saturated atmosphere.

Glutathione Depletion and Evaluation of Drugs as Antioxidants

Experiments were carried out with cultures plated at 30,000~50,000 cells/cm$^2$ in 24-well culture plates (for toxicity and lipid peroxide measurements) or at 136,000 cells/cm$^2$ in 96-well culture plates (for GSH determination). After 8–24 hr, the cultures were switched to culture medium in the absence or presence of the cystine uptake inhibitor glutamate at a final concentration of 10 mM. In order to test drugs for inhibition of oxidative stress, the drug was added together with glutamate (final concentration of solvent was 0.01% hydroxypropyl-β-cylodextrin, 0.1% DMSO). Intracellular glutathione levels were measured after 6~8 hr, lipid peroxides were measured after 14~20 hr, and toxicity and protection were analysed after 48 hr using an LDH assay according to the method of Bergmeyer and Bernt (UV-assay with pyruvate and NADH. In: Methods of Enzymatic Analysis. 1974. H.U. Bergmeyer, ed. Acad. Press, New York, 2nd Ed., pp 574–579).

Determination of GSH Content in C6 Glioma Cultures

GSH levels were analysed by a micromethod, essentially as described by Vandeputte et al. (A microtiterplate assay for total glutathione and glutathione disulfide contents in cultured/isolated cells: performance study of a new miniaturised protocol. 1994. Cell Biol. Toxicol. 10: 415–421), with a modification in the washing and homogenisation procedures. Cells (in 96-well plates) were washed with PBS, were homogenised in 50 µl 10 mM HCl containing 1.3% 5-sulfosalicylic acid, and the homogenate was centrifuged at 1200×g for 10 min at 4° C. Forty µl of the supernatant was transferred to a well of a 96-well plate and 200 µl reagent (1 mM 5,5'-dithiobis-(2-nitrobenzoic acid), 0.34 mM NADPH and 6.3 mM EDTA in 143 mM phosphate buffer pH 7.4) was added. After 5 min equilibration to room temperature the reaction was started by adding 40 µl glutathione reductase (8.5 IU/ml 143 mM phosphate buffer, 6.3 mM EDTA pH 7.4). NADPH oxidation was followed at 414 nm for 5 minutes with a Multiskan MCC/340 (Labsystems), and the change in absorbance (DA) per min was calculated. The glutathione content was deduced from a standard curve ranging from 0.2 to 2 nmol commercial GSH per test (DA/min plotted versus concentration).

Fluorescence Measurement of Intracellular Peroxides

Formation of intracellular peroxides was detected using 6-carboxy-2',7'-dichlorodihydrofluorescin diacetate, di(acetoxymethyl ester) (C-DCDHF, Molecular Probes). C-DCDHF was dissolved in DMSO at a concentration of 10 mM and stored at −70° C. under nitrogen. After exposure of the culture to the glutathione depleting agents, the cells were loaded with 10 µM C-DCDHF for one hour at 37° C. Medium was aspirated off, PBS was added to the cells, and plates were read in a Cytofluor II microplate reader (PerSeptive Biosystems). Excitation and emission wavelength were selected with a 485/530 nm filter pair. The results were expressed in relative fluorescence units/µg protein.

Results

Treatment of C6 glioma cell cultures with 10 mM glutamate for 6 hr or more led to a sharp reduction in intracellular glutathione levels (Table 5). The reduction in glutathione resulted in oxidative stress, as indicated by a ±6-fold increase in toxic intracellular peroxides (Table 5). Ultimately cell death occurs after 16 to 48 hr. Excito-toxicity is not involved in this toxicity, as cytoplasmic LDH release (an index of cellular toxicity) was not prevented by the NMDA antagonist MK801 (data not shown). Under our culture conditions basal LDH release in C6 glioma cultures was 2.7±0.3% of total LDH (mean±SD, n=12), and LDH release after 48 hr treatment with 10 mM glutamate was 93.2±1.3% of total LDH. Both nebivolol and Compound A protected these cultures from cell death with high potency (Table 6). The $IC_{50}$ for protection was found to be approximately 9 nM both for nebivolol and Compound A. This protection was not due to restoration of glutathione levels (Table 5), which remained about half the levels seen in healthy control cells, indicating that protection by both compounds was the result of an interference with GSH-depletion-mediated oxidative stress. Evaluation of intracellular peroxides, showed that both nebivolol and compound A inhibited the glutamate-mediated increase in peroxidation (Table 5).

Conclusion

This is clear in vitro evidence that both compounds act in cell culture as potent antioxidants; they protect cells from oxidative stress-mediated cell death, as they inhibit the oxidative stress-mediated increase in toxic intracellular peroxides.

TABLE 5

Inhibition of glutathione depletion-mediated intercellular peroxidation in C6 glioma cells

| Compound | GSH levels pmol/well (mean ± SD, 6) | Intracellular peroxides Relative fluorescence units/ µg protein (mean ± SD, n) |
|---|---|---|
| Solvent | 90 ± 9 | 86 ± 16 (12) |
| Glutamate, 10 mM | 296 ± 26 | 525 ± 57 (12) |
| +Compound A, 1 µM | 301 ± 12 | 137 ± 8 (3) |
| +Nebivolol, 1 µM | 301 ± 12 | 155 ± 13 (3) |

TABLE 6

Inhibition of glutathione depletion-mediated oxidative stress (toxicity) in C6 glioma cell

| Compound | Protection $IC_{50}$, nM (mean ± SD, n = 3) |
|---|---|
| Compound A | 8.6 ± 0.2 |
| Nebivolol | 9.1 ± 0.1 |

What is claimed is:

1. A method of treating patients suffering from aging of or degenerative diseases of the nervous system which are associated with oxidative stress, by administering to said patients an amount of an α,α'-iminobis(methylene)bis-[2-chromanmethanol] derivative having the formula (I) effective in improving, halting, retarding or palliating the course and/or effects of said aging and degenerative diseases (I)

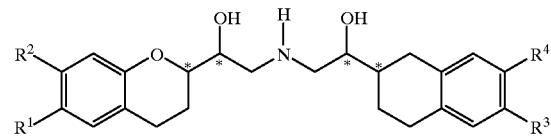

wherein $R^1$ and $R^3$ each independently represent fluoro, hydroxy or hydrogen; $R^2$ and $R^4$ each independently represent hydrogen or hydroxy; and each asterisk indicates a stereogenic center.

2. The method of claim 1, wherein the disease to be treated comprises neuronal loss from the peripheral nervous system which is associated with oxidative damage or injury such as in thromboembolic stroke, cerebral stroke, haemorrhagic stroke, cerebral ischemia, cerebral vasospasm, cerebral aging, cerebral or spinal trauma, cardiac arrest, arterial hypotension, cardiac or pulmonary surgery, severe hypoglycaemia, anoxia, hypoxia, or perinatal asphyxia.

3. The method of claim 1, wherein the disease to be treated comprises neurodegenerative disorders wherein oxidative metabolic processes play a role such as Huntington's chorea, Alzheimer's disease, senile dementia, Pick's disease, Korsakoff's disease, olivoponto cerebellar atrophy, amyotophic lateral sclerosis, Parkinson's disease, Down's syndrome, glutaric acidaemia, epilepsy, convulsive states, multi-infarct dementia, or viral-infection induced neurodegeneration such as neuro-AIDS encompassing dementia, cognitive difficulties, neuro- and myopathies associated with HIV infection, rabies, measles and/or tetanus.

4. The method according to claim 1, wherein the compound of formula (I) is nebivolol.

5. The method according to claim 4, wherein the compound of formula (I) is used for the manufacture of a pharmaceutical composition adapted for oral administration.

6. The method according to claim 5, wherein the daily dose of nebivolol ranges from 0.1 to 20 mg.

7. The method according to claim 6, wherein the daily dose is given in a single administration.

* * * * *

UNITED STATES PATENT AND TRADEMARK OFFICE
CERTIFICATE OF CORRECTION

PATENT NO.    : 6,075,046
DATED         : June 13, 2000
INVENTOR(S)   : de Chaffoy de Courcelles et al.

It is certified that error appears in the above-identified patent and that said Letters Patent is hereby corrected as shown below:

Column 14,
Line 45, replace

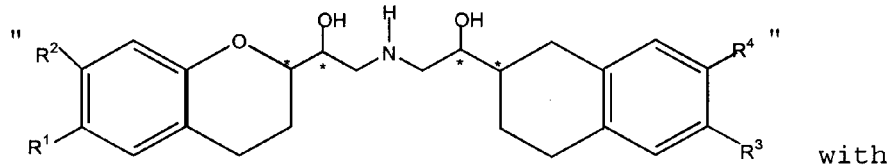 with

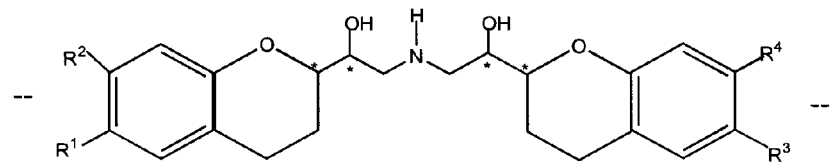 --

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,075,046
DATED : June 13, 2000
INVENTOR(S) : de Chaffoy de Courcelles et al.

It is certified that error appears in the above-identified patent and that said Letters Patent is hereby corrected as shown below:

Title page,
Item [63], Related U.S. Application Data, please insert: -- Continuation of application serial no. 08/860,238, filed June 16, 1997, now patent no. 5,874,461. --
Insert items:
-- [22] PCT Filed: December 21, 1995
   [86] PCT No.: PCT/EP95/05174
      §371 Date: Jun. 16, 1997
      §102(e) Date: Jun. 16, 1997
   [87] PCT Pub. No.: WO/96/19987
      PCT Pub. Date: Jul. 4, 1996 --

Signed and Sealed this

Third Day of May, 2005

JON W. DUDAS
*Director of the United States Patent and Trademark Office*